(12) United States Patent
Sugasawa (10) Patent No.: US 9,329,116 B2
(45) Date of Patent: May 3, 2016

(54) PARTICLE SIZE DISTRIBUTION MEASURING DEVICE

(71) Applicant: HORIBA, Ltd., Kyoto (JP)

(72) Inventor: Hirosuke Sugasawa, Kyoto (JP)

(73) Assignee: HORIBA, LTD. (JP)

( * ) Notice: Subject to any disclaimer, the term of this patent is extended or adjusted under 35 U.S.C. 154(b) by 31 days.

(21) Appl. No.: 14/301,822

(22) Filed: Jun. 11, 2014

(65) Prior Publication Data

US 2014/0368820 A1     Dec. 18, 2014

(30) Foreign Application Priority Data

Jun. 17, 2013   (JP) .................................. 2013-126911

(51) Int. Cl.
   *G01N 15/02*         (2006.01)
(52) U.S. Cl.
   CPC .................................. *G01N 15/0211* (2013.01)
(58) Field of Classification Search
   USPC ............... 356/335–343, 72, 319; 702/128, 23
   See application file for complete search history.

(56) References Cited

U.S. PATENT DOCUMENTS

| | | | |
|---|---|---|---|
| 5,619,324 A | 4/1997 | Harvill et al. | |
| 6,252,658 B1 * | 6/2001 | Togawa | G01N 15/0211 356/335 |
| 6,692,532 B1 * | 2/2004 | Healy | A61L 24/0068 623/23.51 |
| 7,180,592 B2 * | 2/2007 | Yoshioka | G01N 15/0205 356/336 |
| 7,187,441 B1 * | 3/2007 | Sevick-Muraca | G01N 21/49 356/336 |
| 7,242,473 B2 * | 7/2007 | Togawa | G01N 15/0205 356/335 |
| 2004/0011975 A1 * | 1/2004 | Nicoli | G01N 15/0227 250/574 |
| 2009/0013905 A1 * | 1/2009 | VanRemortel | B02C 19/065 106/439 |
| 2009/0091756 A1 * | 4/2009 | Yamaguchi | G01N 15/0205 356/336 |
| 2009/0222218 A1 * | 9/2009 | Chamberlin | G01J 3/10 702/23 |
| 2011/0181869 A1 * | 7/2011 | Yamaguchi | G01N 15/0205 356/72 |
| 2011/0213581 A1 * | 9/2011 | Sugasawa | G01N 15/0211 702/128 |

FOREIGN PATENT DOCUMENTS

| | | | |
|---|---|---|---|
| JP | 2010101635 A | | 5/2010 |
| WO | 98/20323 A1 | | 5/1998 |

OTHER PUBLICATIONS

Search Report corresponding to UK Patent Application No. GB1410618.1, Date of Issuance: Dec. 10, 2014.
Tang, H, "Retrieval of Spherical Particle Size Distribution with an Improved Tikhonov Iteration Method", Thermal Science, 2012, vol. 16, No. 5, pp. 1400-1404.

* cited by examiner

*Primary Examiner* — Sang Nguyen
(74) *Attorney, Agent, or Firm* — Cantor Colburn LLP (57) ABSTRACT

The particle size distribution measuring device 1 is so configured to calculate the particle size distribution with repeating several times a process to give the particle size distribution calculated by means of one iterative solver to the other iterative solver as an imaginary solution and to update the calculated particle size distribution as a new particle size distribution.

7 Claims, 5 Drawing Sheets

PARTICLE SIZE DISTRIBUTION MEASURING DEVICE

CROSS REFERENCE TO RELATED APPLICATIONS

The present invention claims priority under 35 U.S.C. §119 to Japanese Application No. 2013-126911 filed Jun. 17, 2013, the entire content of which is incorporated herein by reference.

FIELD OF THE ART

This invention relates to a particle size distribution measuring device that calculates a particle size distribution of a particle group based on a characteristic of a secondary light (for example, a space intensity distribution of a diffractive light/a scattered light, the Doppler shift or the like) that is produced when an inspection light is irradiated on the particle group.

BACKGROUND ART

A conventional so-called static particle size distribution measuring device calculates, as shown in the patent document 1, a particle size distribution based on the following expression (Expression 1).

$$s = Kq \quad \text{(Expression 1)}$$

where "s" is a vector that expresses a space intensity distribution of a secondary light obtained from output signals of multiple light sensors arranged dispersedly around a particle group, "q" is a vector that expresses a particle size distribution, and "K" is a coefficient matrix that is uniquely determined by a physical property concerning a refractive index of the particle group and an arranged position of the light sensor.

Here, since what to be obtained is the vector (q) that expresses the particle size distribution and the vector (q) is in the right side of the expression, an inverse problem is to be solved.

Then, conventionally, the vector (q) (the particle size distribution) is calculated by the use of a previously determined single iterative solver such as, for example, the Twomey iterative method. The iterative solver is to first give an imaginary solution of the particle size distribution, to calculate an imaginary light intensity distribution by substituting the imaginary solution for the above-mentioned expression 1, to update the imaginary solution one by one so as to make the imaginary light intensity distribution approach the actually measured space intensity distribution (hereinafter also called as a real space intensity distribution) and to calculate the resultantly obtained imaginary solution as the particle size distribution.

PRIOR ART DOCUMENTS

Patent Document

Patent document 1: Japanese Unexamined Patent Application Publication No. 2010-101653

DISCLOSURE OF THE INVENTION

Problems to be Solved by the Invention

However, in accordance with the above-mentioned conventional particle size distribution measuring device, a problem might arise that it is not possible to calculate the particle size distribution with high accuracy depending on how an initial imaginary solution is given or a mode (for example, a distribution having multiple peaks) of a real particle size distribution, or a solution of the particle size distribution vibrates or diverges such that a peak shifts every time a number of repetition of calculation is changed.

Similar problem is common to all of the particle size distribution measuring devices that obtain the particle size distribution by solving an inverse problem based on the other characteristic of the secondary light including, including a so-called dynamic particle size distribution measuring device that obtains the particle size distribution by solving an inverse problem from the Doppler shift of the secondary light.

Then the present claimed invention intends to solve all of the problems and a main object of this invention is to provide a particle size distribution measuring device that can calculate the particle size distribution accurately and stably.

Means to Solve the Problems

More specifically, the particle size distribution measuring device in accordance with this invention comprises a light source that irradiates an inspection light on a dispersed particle group, multiple light receiving parts that receive a secondary light produced when the inspection light is irradiated on the particle group and an arithmetic circuit that calculates a particle size distribution of the particle group based on a characteristic of the secondary light (hereinafter called as a real secondary light characteristic) obtained from an output signal of each of the light receiving parts, and the arithmetic circuit uses an iterative solver (called as an iterative solver even though the update is conducted once) that updates an imaginary solution once or multiple times in order to make a characteristic of an imaginary secondary light (hereinafter called as an imaginary secondary light characteristic) calculated based on the imaginary solution of the particle size distribution approach the real secondary light characteristic and that calculates the obtained imaginary solution as the particle size distribution, and is characterized by that the arithmetic circuit repeats once or multiple times a process to update the particle size distribution calculated by the use of one iterative solver with a new particle size distribution calculated by giving the calculated particle size distribution to the other iterative solver as the imaginary solution.

In accordance with this arrangement, since the particle size distribution is calculated by the use of the different multiple iterative solvers, it is possible to obtain the particle size distribution that is closer to the true solution. In addition, it is possible to largely reduce a frequency that the solution of the particle size distribution becomes unstable.

In order to make it possible to calculate the particle size distribution with higher accuracy, it is preferable that the arithmetic circuit calculates multiple particle size distributions by repeating once or several times a process to calculate the multiple particle size distributions by giving multiple imaginary solutions each of which differs respectively to the one iterative solver and to update one part or all of the multiple particle size distributions with multiple new particle size distributions calculated by giving the calculated one part or all of the multiple particle size distributions to the other iterative solver as the imaginary solution, and outputs the particle size distribution that is the best evaluated when applied to a prescribed evaluating method among the multiple calculated particle size distributions.

As a concrete embodiment represented is that the arithmetic circuit selects the best evaluated particle size distribution when applied to the above-mentioned evaluating method and a succeeding predetermined number of particle size distributions among the multiple particle size distributions calculated by the above-mentioned one iterative solver and gives the selected particle size distributions to the other iterative solver as the imaginary solution.

Since the evaluating method is determined for each of the iterative solvers, the evaluation value of the particle size distribution calculated by the different iterative solvers can be said to be the individual evaluation value that is independent each other, and cannot be compared each other because it has a different standard respectively. In order to make it possible to compare the evaluation values of the particle size distribution, it is preferable to determine the individual evaluation value obtained respectively by applying a predetermined standard particle size distribution to each of the evaluating methods as a representative value for each of the evaluating methods, and to normalize the individual evaluation value obtained for the particle size distribution to be evaluated by the use of the representative value of the evaluating method concerned.

As the standard particle size distribution represented is a uniform particle size distribution.

Effect of the Invention

In accordance with the present claimed invention having the above-mentioned arrangement, since the particle size distribution is calculated by the use of the multiple different iterative solvers, it is possible to obtain the particle size distribution that is closer to the true solution, and it is also possible to largely reduce frequency that the solution of the particle size distribution becomes unstable.

BEST MODES OF EMBODYING THE INVENTION

One embodiment of this invention will be explained with reference to drawings.

Figure 1:
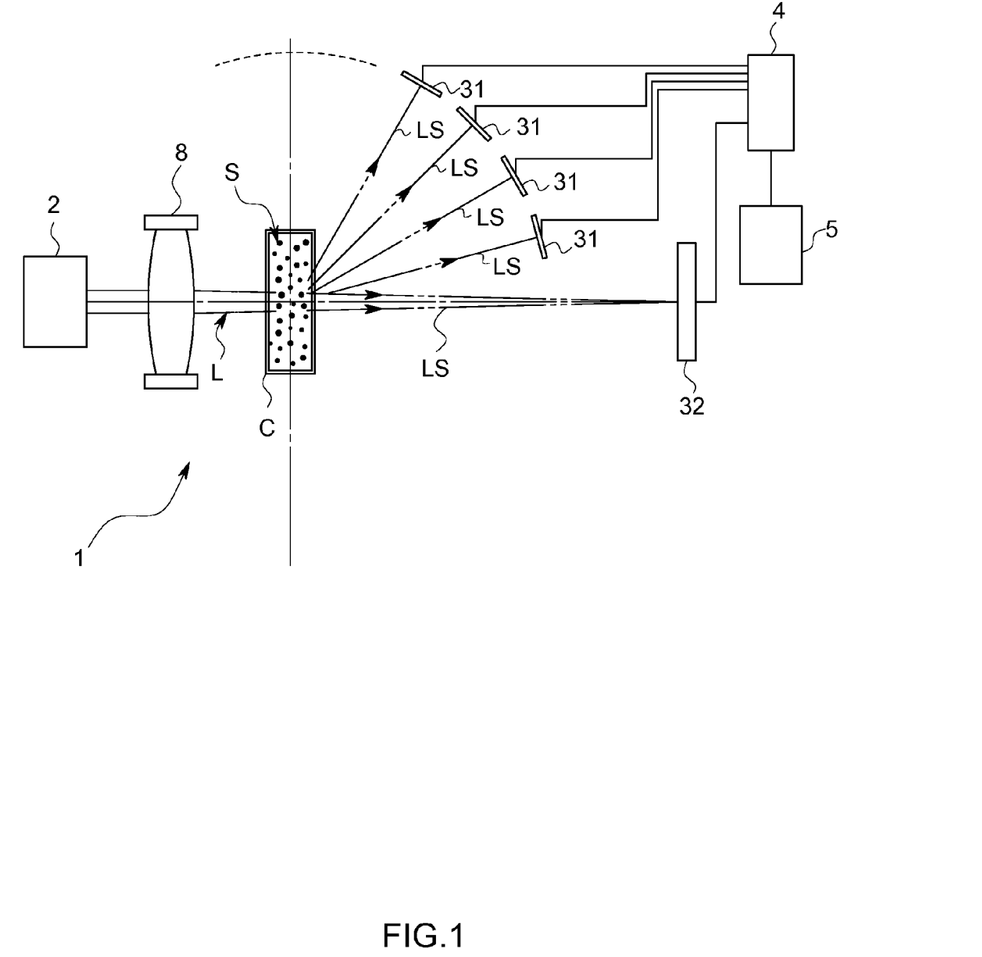
FIG. 1 is a pattern overall configuration view of a particle size distribution measuring device in accordance with one embodiment of this invention.

A particle size distribution measuring device 1 in accordance with this embodiment is, as shown in FIG. 1, to measure a particle size distribution based on the MIE scattered light theory by detecting a characteristic of a diffracted/scattered light (LS) as being a secondary light that is produced when an inspection light (L) is irradiated on a dispersed particle group (S), namely a space distribution of the light intensity.

The code (C) in FIG. 1 is a cell that houses the particle group (S) as being a measurement object that is dispersed in a dispersion medium. The dispersion medium is generally water in a wet case and air in a dry case.

The code 2 in FIG. 1 is a light source that irradiates the inspection light (L) on the cell (C). For example, a semiconductor laser that irradiates a coherent laser light is used as the light source in this embodiment.

The codes 31 and 32 are light sensors such as a photomultiplier, a CCD or a CMOS as being a light receiving part arranged around the cell (C), and detect the light intensity per every angle of the diffracted light/scattered light (LS) that is produced by the inspection light (L) that falls on the particle group (S).

The code 8 is a convex lens wherein the inspection light (L) is set to converge on a center of a light receiving surface of the light sensor 32.

The code 4 is a signal processing circuit that comprises a buffer to conduct a process of transformation and an amplifier or the like that receives an output signal from each of the light sensors 31, 32.

The code 5 is an arithmetic circuit that calculates a particle size distribution of the particle group (S) based on a space intensity distribution (corresponds to a real secondary light characteristic in claims, and hereinafter is called as a real light intensity distribution) of the secondary light obtained from a value of each output signal processed by the signal processing circuit 4. The arithmetic circuit 5 is so-called a computer comprising a CPU and a memory (a memory medium), and functions as a solver executing part 51 (i.e., an iterative solver), an evaluating part 52 and a selecting part 53 as shown in FIG. 2 by cooperatively working with the CPU and its peripheral devices based on programs stored in a predetermined area of the memory.

The solver executing part 51 calculates the particle size distribution by solving an expression (the expression 1) expressed in the prior art example on "q".

Figure 3:
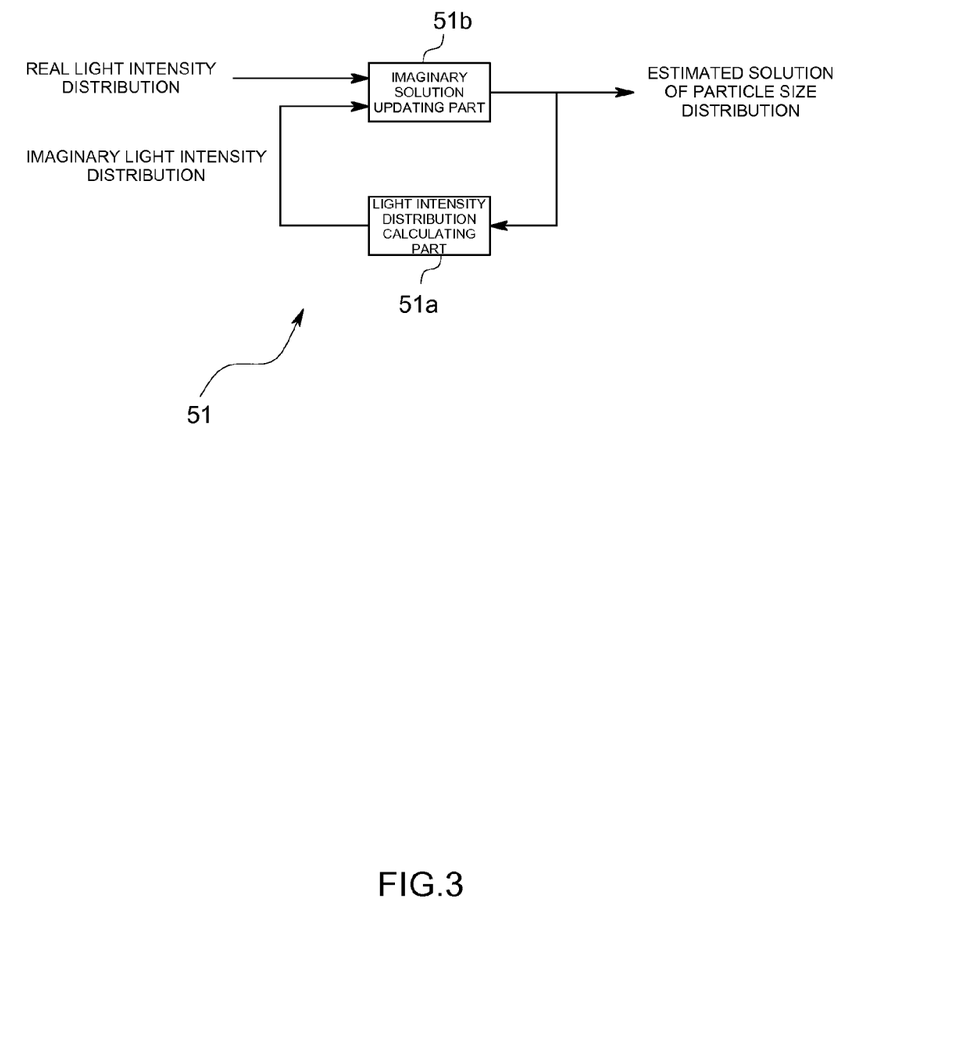
FIG. 3 is a function block diagram of a solver executing part in this embodiment.

Explained more concretely, the solver executing part 51 comprises, as shown in FIG. 3, a light intensity distribution calculating part 51a that calculates an imaginary space intensity distribution of the secondary light (corresponds to the imaginary secondary light characteristic in claims, and hereinafter is called as the imaginary light intensity distribution) calculated based on an imaginary solution of the particle size distribution and an imaginary solution updating part 51b that updates the imaginary solution in order to make the imaginary light intensity distribution approach the above-mentioned real light intensity distribution, and calculates the imaginary solution obtained by repeatedly conducting the movement of the light intensity distribution calculating part 51a and the imaginary solution updating part 51b alternatively as the particle size distribution. A number of the repetition may be a previously determined constant number or the repetition may be terminated at a time when an evaluation value, to be described later, exceeds a predetermined threshold value.

Figure 2:
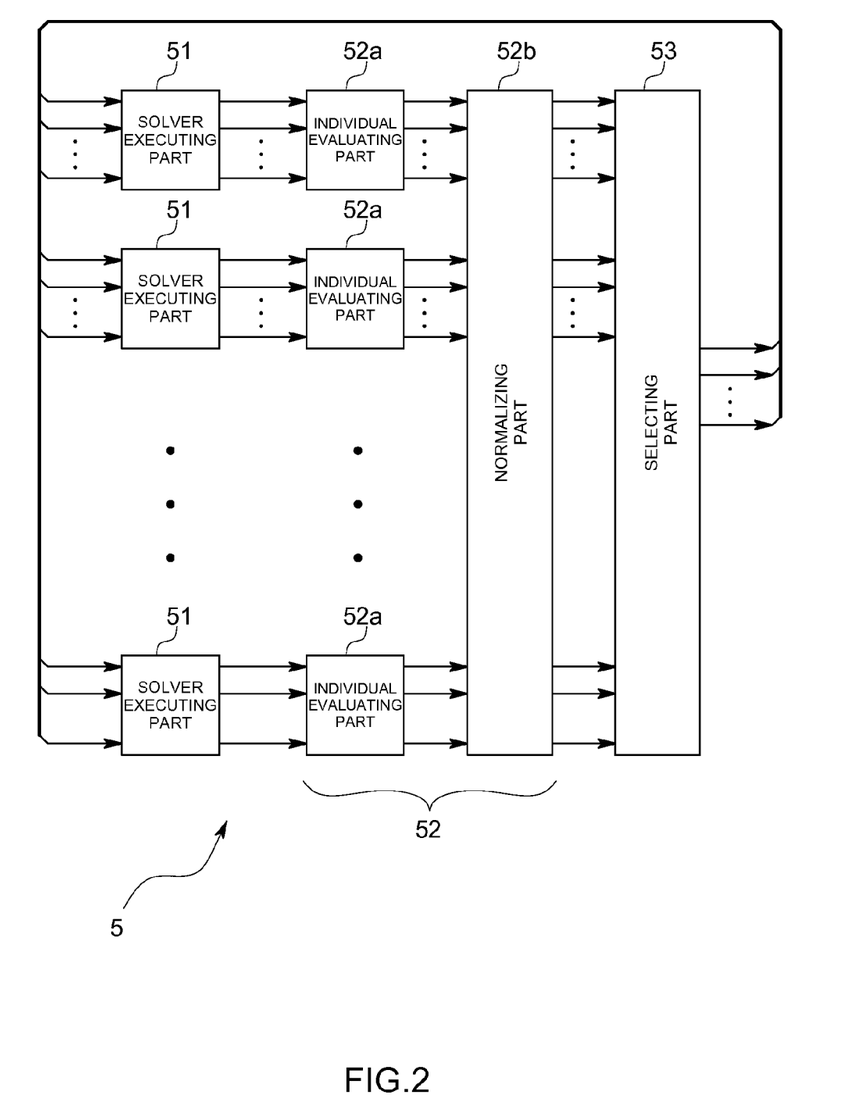
FIG. 2 is a function block diagram of an arithmetic circuit in accordance with this embodiment.

Meanwhile, in this embodiment, multiple solver executing parts 51 whose solution principle differs each other are provided as shown in FIG. 2. As the solution principles used in this embodiment represented are the MRNSD method, the SymmLQ method, the HyBR method, the CGL method, the GMRES method, the QMR method, and the Twomey iterative method or the like. Each of the solution principles is stored in the above-mentioned memory in a form of for example, a numerical expression.

In addition, the solver executing part 51 can receive multiple imaginary solutions and can calculate each of the particle size distributions by computing each imaginary solution in parallel or in turn.

The initial imaginary solution is necessary in order to initiate the movement of the solver executing part 51. The multiple initial imaginary solutions are previously stored in a predetermined area of the memory and the solver executing part 51 obtains each of the initial imaginary solutions at a time of initiating the movement. One example of the initial imaginary solution is shown in FIG. 4.

The evaluating part 52 calculates an evaluation value indicating a probability of the imaginary solution. The evaluating part 52 comprises an individual evaluating part 52a that is provided correspondingly with each solver executing part 51, and a normalizing part 52b that normalizes multiple individual evaluation values output by the individual evaluating part 52a and that outputs the normalized individual evaluation values as the normalized evaluation values that can be directly compared.

The individual evaluating part 52a calculates the individual evaluation value as being a value evaluated by means of an evaluating method determined for each of the solution principles. The evaluating method is stored in the above-mentioned memory in a form of for example, a numerical expression. The individual evaluation value is fundamentally a value indicating a distance between an imaginary light intensity distribution calculated by the imaginary solution to be evaluated and a real light intensity distribution, and is calculated by the use of an index that differs for every solver principle. For example, for the individual evaluating part 52a that uses the Twomey iterative method as the solver principle, a residual sum of squares is output as the individual evaluation value. For the individual evaluating part 52a that uses the MRNSD method as the solver principle, likelihood is output as the individual evaluation value. Each solver principle and evaluating method corresponding to each solver are previously stored in the memory as, for example, a numerical expression, and the individual evaluating part 52 refers to the memory in case of calculating the evaluation value.

Figure 4:
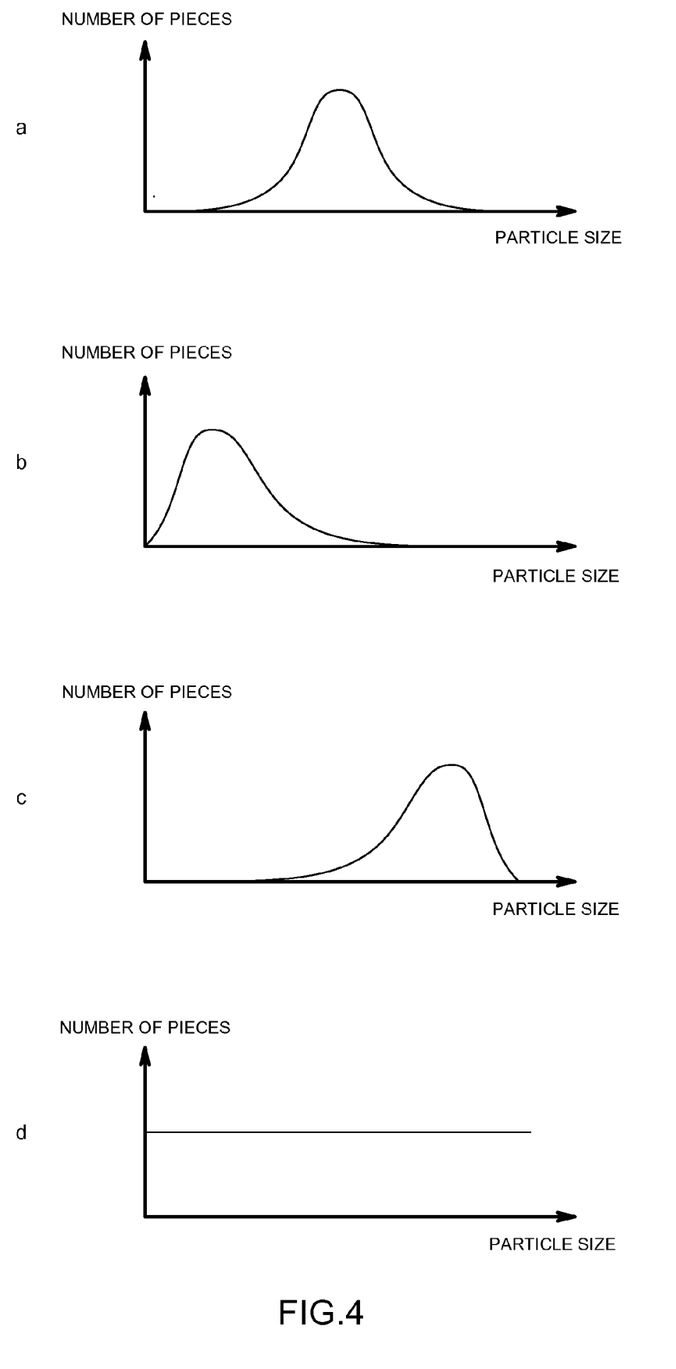
FIG. 4 is an illustration view of an initial imaginary solution in this embodiment.

The normalizing part 52b uses the individual evaluation value at a time when a previously determined prescribed standard particle size distribution (for example, an uniform particle size distribution wherein a number of particles for each particle size is equal as shown in FIG. 4 (d)) is evaluated by the individual evaluating part 52a as a representative value, and a ratio of the individual evaluation value at a time when the imaginary solution to be evaluated is evaluated by the individual evaluating part 52a to the representative value or a correlation value of the ratio is output as the normalized evaluation value.

In this embodiment, the normalized evaluation value is obtained by the use of, for example, the following expression (expression 2). In this case, 1 is the best evaluated (the imaginary solution is most likely) and the smaller than 1 the value is, the worse the evaluation becomes.

$$E = \frac{MaxErr - Err}{MaxErr} \qquad \text{Expression 2}$$

where, E is the normalized evaluation value, MaxErr is the representative value and Err is the individual evaluation value.

The selecting part 53 compares each of the normalized evaluation value calculated by the normalizing part 52b and selects and outputs the best evaluated normalized evaluation value and a subsequent predetermined number of the normalized evaluation value in order. The number of the output normalized evaluation value is set to be equal to a number of the initial imaginary solution given to the solver executing part 51.

Next, a movement of the particle size distribution measuring device 1 having the above-mentioned arrangement will be explained with focusing on a movement of the arithmetic circuit 5.

When the inspection light (L) is irradiated on the particle group (S) to be measured, the arithmetic circuit 5 calculates the real light intensity distribution as being the light intensity distribution of the diffracted light/the scattered light (the light intensity distribution vector (s)) based on the output signal of each light sensor 31, 32.

Next, each solver executing part 51 obtains the multiple initial imaginary solutions stored in the memory in a form of a numerical formula or a table respectively, for example as shown in FIG. 4 a~d (step 1)

Then, each solver executing part 51 calculates the particle size distribution of the same number as that of the imaginary solution while referring to the real light intensity distribution (step 2). The movement (the calculation) of each solver executing part 51 may be conducted in parallel or in order.

The individual evaluation value is given to each of the particle size distributions by the individual evaluating part 52a, and each of the individual evaluation values is furthermore converted to the normalized evaluation value by the normalizing part 52b (step 3).

More specifically, if there are "N" pieces of the solver executing parts 51 and "M" pieces of the imaginary solutions (each of "N" and "M" is an integral number, 1 or more than 1), "N" times "M" pieces of the particle size distributions are calculated by the movement of each solver executing part 51 and the normalized evaluation value is correlated to each of the particle size distributions respectively and stored in the memory.

Next, the selecting part 53 extracts the normalized evaluation values from the best evaluated one to the "M"th (not necessarily be the "M"th) one, and the particle size distribution correlated to the normalized evaluation value is given to each of the solver executing part 51 as a new imaginary solution (step 4). At this time, there also exists the solver executing part 51 to which the particle size distribution that is calculated by itself is given again as the initial imaginary solution.

Then the above-mentioned step 2~step 4 are repeated by a previously determined number of times.

As this result, the arithmetic circuit 5 outputs the best evaluated normalized evaluation value among the obtained "M" pieces of the particle size distributions as the final calculated result of the particle size distribution.

In accordance with the particle size distribution measuring device having the above-mentioned arrangement, since the particle size distribution is calculated by the use of the plurality of different iterative methods, it is possible to obtain the particle size distribution that is nearer to the true value of the solution. In addition, it is also possible to drastically reduce a situation wherein the solution of the particle size distribution diverges or vibrates. Furthermore, since there are a lot of parts where a parallel calculation is conducted, it does not take time uselessly to calculate the particle size distribution compared with a conventional case. If a CPU that can conduct parallel calculation is used as the CPU, the time required for calculation is rather shortened compared with a conventional device.

The present claimed invention is not limited to the above-mentioned embodiment.

For example, the one that outputs the given imaginary solution as the particle size distribution as it is may be added to one of the solver executing parts 51. In accordance with this arrangement, even if in a case that the imaginary solution is updated successively to a worse evaluated solution by all of the other solver executing parts 51, the imaginary solution by the solver executing part 51 concerned is kept as the original value without being updated. As a result of this, the evaluated value is accordingly positioned at the highest position. Then, the imaginary solution concerned is selected by the selecting part 53 without fail so that it is possible to securely eliminate a case that the more times the calculation is conducted, the more the selected solution is deviated from the true solution.

For example, a number of repeating the step 2 through the step 4 is not necessarily the predetermined number, and the repetition may be stopped at a time when any of the normalized evaluated value among the particle size distributions obtained by executing the step 4 exceeds the predetermined threshold value and becomes better, or at a time when the best normalized evaluated value stops improving by an amount more than a predetermined amount.

The imaginary solution received (or obtained) by the solver executing part 51 may be one.

Figure 5:
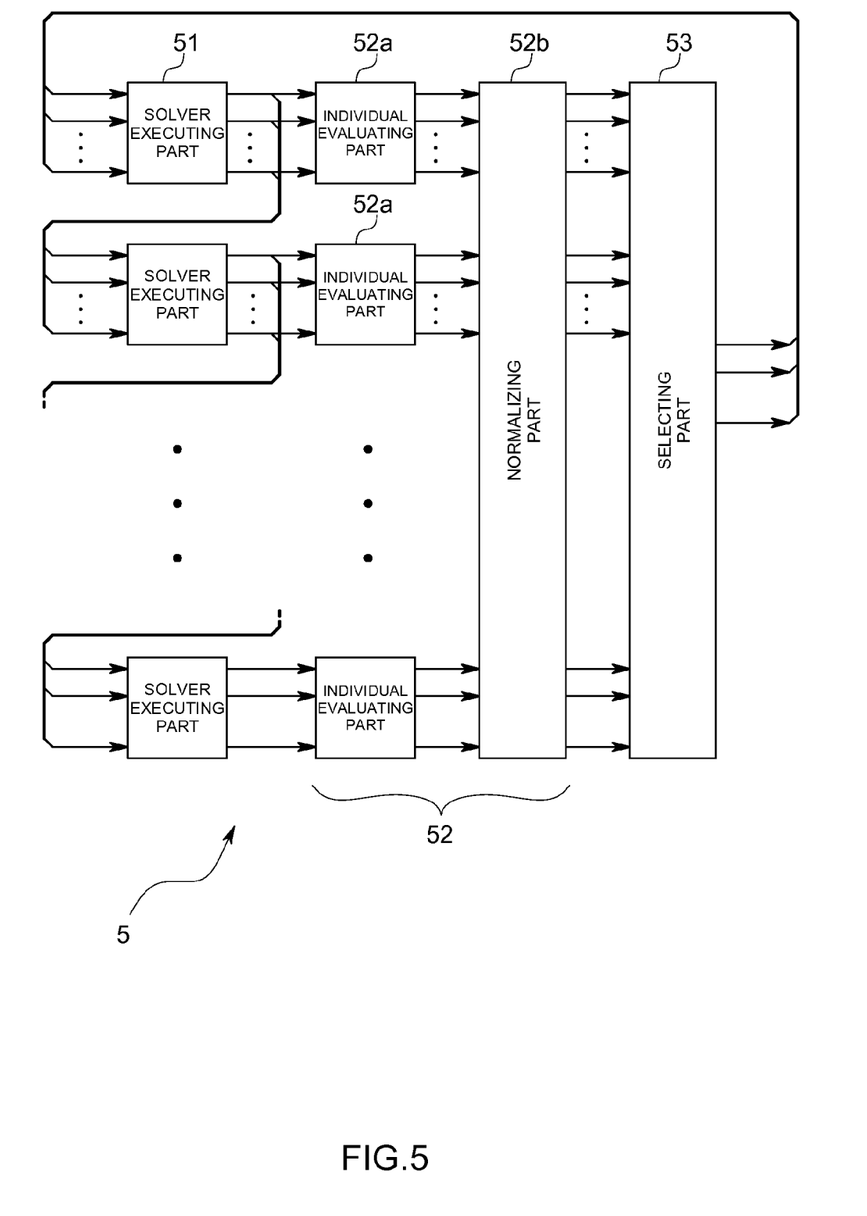
FIG. 5 is a function block diagram of an arithmetic circuit in accordance with another embodiment of this invention.

In the above-mentioned embodiment, the particle size distribution selected by the selecting part 53 is given in parallel as the imaginary solution to the multiple solver executing parts 51, however, as shown in FIG. 5, the particle size distribution calculated by a certain solver executing part 51 may be given to one of the other solver executing parts 51 and may be repeated. The number of repetition may be a certain times similar to the above-mentioned embodiment, or the repetition may be stopped at a time when the normalized evaluated value exceeds the predetermined threshold value and becomes better, or at a time when the normalized evaluated value stops improving by an amount more than a predetermined amount.

In addition, the present claimed invention may be applied to a so-called dynamic particle size distribution measuring device. In this case, the secondary light characteristic is obtained from the Doppler shift of the secondary light.

In addition, it is a matter of course that the present claimed invention is not limited to the above-mentioned embodiment and may be variously modified without departing from a spirit of the invention.

EXPLANATION OF CODES

S . . . particle group
1 . . . particle size distribution measuring device
2 . . . light source (semiconductor laser)
31, 32 . . . light receiving part (light sensor)
5 . . . arithmetic circuit

The invention claimed is:

1. A particle size distribution measuring device for use with a dispersed particle group, the particle size distribution measuring device comprising:
a light source that structured to irradiate an inspection light on the dispersed particle group;
a light receiving part structured to receive a secondary light produced when the inspection light is irradiated on the particle group; and
an arithmetic circuit structured to calculate a particle size distribution of the particle group based on a characteristic of the secondary light (hereinafter called a real secondary light characteristic) obtained from an output signal of the light receiving part, wherein
the arithmetic circuit comprises an iterative solver that structured to update more than once an imaginary solution in order to make a characteristic of an imaginary secondary light (hereinafter called an imaginary secondary light characteristic) calculated based on the imaginary solution of the particle size distribution approach the real secondary light characteristic and structured to calculate the obtained imaginary solution as the particle size distribution, and the arithmetic circuit is structured to repeat more than once a process to update the particle size distribution calculated by the use of one iterative solver with a new particle size distribution calculated by giving the calculated particle size distribution to the other iterative solver, that is different from the one iterative solver, as the imaginary solution.

2. The particle size distribution measuring device described in claim 1, wherein
the arithmetic circuit calculates the multiple particle size distributions by repeating more than once a process to calculate the multiple particle size distributions by giving multiple imaginary solutions each of which differs respectively to the one iterative solver and to update one part or all of the multiple particle size distributions with multiple new particle size distributions calculated by giving the calculated one part or all of the multiple particle size distributions to the other iterative solver as the imaginary solution, and outputs the particle size distribution that is the best evaluated when applied to a prescribed evaluating method among the multiple calculated particle size distributions.

3. The particle size distribution measuring device described in claim 2, wherein
the arithmetic circuit selects the best evaluated particle size distribution when applied to the above-mentioned evaluating method and a succeeding predetermined number of particle size distributions among the multiple particle size distributions calculated by the use of the above-mentioned one iterative solver and gives the selected particle size distributions to the other iterative solver as the imaginary solution.

4. The particle size distribution measuring device described in claim 2, wherein
the evaluating method is determined for each of the iterative solvers, and each of the evaluating methods outputs an individual evaluation value as being its own evaluation value to the particle size distribution calculated by the corresponding iterative solver, and is characterized by
determining the individual evaluation value obtained respectively by applying a predetermined standard particle size distribution to each of the evaluating methods as a representative value for each of the evaluating methods, and normalizing the individual evaluation value obtained for the particle size distribution to be evaluated by the use of the representative value of the evaluating method concerned.

5. The particle size distribution measuring device described in claim 4, wherein
the standard particle size distribution is uniform.

6. A particle size distribution measuring method that irradiates an inspection light from a light source on a dispersed particle group and that calculates a particle size distribution of the particle group based on a characteristic of a secondary light (hereinafter called as a real secondary light characteristic) produced when the inspection light is irradiated on the particle group and received by a light receiving part, the method comprising:
using an iterative solver that updates several times an imaginary solution in order to make a characteristic of an imaginary secondary light (hereinafter called as an imaginary secondary light characteristic) calculated based on the imaginary solution of the particle size distribution approach the real secondary light characteristic and that calculates the obtained imaginary solution as the particle size distribution, repeating more than once a process that updates the particle size distribution calculated by the use of one iterative solver with a new particle size distribution calculated by giving the calculated particle size distribution to the other iterative solver, that is different from the one iterative solver, as the imaginary solution.

7. A non-transient computer-readable media comprising computer executable instructions that, when executed by a computer in conjunction with a particle size distribution measuring device comprising a light source that irradiates an inspection light on a dispersed particle group, multiple light receiving parts that receive a secondary light produced when the inspection light is irradiated on the particle group and an arithmetic circuit that calculates a particle size distribution of the particle group based on a characteristic of the secondary light (hereinafter called as a real secondary light characteristic) obtained from an output signal of each of the light receiving parts; cause the computer to perform:

executing an iterative solver that updates more than once an imaginary solution in order to make a characteristic of an imaginary secondary light (hereinafter called as an imaginary secondary light characteristic) calculated based on the imaginary solution of the particle size distribution approach the real secondary light characteristic and that calculates the obtained imaginary solution as the particle size distribution, and repeating more than once a process of updating the particle size distribution calculated by means of one iterative solver with a new particle size distribution calculated by giving the calculated particle size distribution to the other iterative solver, that is different from the one iterative solver, as the imaginary solution.

* * * * *